US012778863B2

(12) United States Patent
Iida et al.

(10) Patent No.: US 12,778,863 B2
(45) **Date of Patent: *Nov. 3, 2026**

(54) TOPICAL SKIN PREPARATION COMPOSITION

(71) Applicant: KAO CORPORATION, Tokyo (JP)

(72) Inventors: Masayuki Iida, Odawara (JP); Yukihiro Miyazaki, Odawara (JP)

(73) Assignee: KAO CORPORATION, Tokyo (JP)

(*) Notice: Subject to any disclaimer, the term of this patent is extended or adjusted under 35 U.S.C. 154(b) by 529 days.

This patent is subject to a terminal disclaimer.

(21) Appl. No.: 17/995,277

(22) PCT Filed: Mar. 22, 2021

(86) PCT No.: PCT/JP2021/011783

§ 371 (c)(1),
(2) Date: Sep. 30, 2022

(87) PCT Pub. No.: WO2021/200353

PCT Pub. Date: Oct. 7, 2021

(65) Prior Publication Data

US 2023/0149272 A1 May 18, 2023

(30) Foreign Application Priority Data

Apr. 1, 2020 (JP) ................................ 2020-066247

(51) Int. Cl.

| | |
|---|---|
| ***A61K 8/25*** | (2006.01) |
| ***A61K 8/31*** | (2006.01) |
| ***A61K 8/34*** | (2006.01) |
| ***A61K 8/60*** | (2006.01) |
| ***A61K 8/891*** | (2006.01) |
| ***A61Q 19/08*** | (2006.01) |

(52) U.S. Cl.

CPC ................. *A61K 8/25* (2013.01); *A61K 8/31* (2013.01); *A61K 8/345* (2013.01); *A61K 8/60* (2013.01); *A61K 8/891* (2013.01); *A61Q 19/08* (2013.01)

(58) Field of Classification Search

None

See application file for complete search history.

(56) References Cited

U.S. PATENT DOCUMENTS

| | | | | |
|---|---|---|---|---|
| 2010/0190950 | A1* | 7/2010 | Tetsuka ................. | B01D 71/44 528/33 |
| 2011/0301247 | A1* | 12/2011 | Hayakawa ............ | A61Q 17/04 528/33 |
| 2015/0272858 | A1 | 10/2015 | Hayashi et al. | |
| 2017/0224608 | A1 | 8/2017 | Fujiyama et al. | |
| 2021/0196586 | A1* | 7/2021 | Farran ...................... | A61K 8/26 |

FOREIGN PATENT DOCUMENTS

| | | | |
|---|---|---|---|
| CN | 102666664 | A | 9/2012 |
| CN | 104546512 | A | 4/2015 |
| CN | 105745288 | A | 7/2016 |
| EP | 2 444 062 | A2 | 4/2012 |
| EP | 2 647 366 | A2 | 10/2013 |
| EP | 3 175 841 | A1 | 6/2017 |
| EP | 3 308 767 | A1 | 4/2018 |
| JP | 2001-278729 | A | 10/2001 |
| JP | 2004-26731 | A | 1/2004 |
| JP | 2009-173653 | A | 8/2009 |
| JP | 2010-229094 | A | 10/2010 |
| JP | 2012-17317 | A | 1/2012 |
| JP | 2016-33130 | A | 3/2016 |
| JP | 2019-131489 | A | 8/2019 |
| WO | WO 2014/054693 | A1 | 4/2014 |

OTHER PUBLICATIONS

Extended European Search Report issued Mar. 20, 2024 in European Patent Application No. 21781276.7, 11 pages.
International Search Report issued May 25, 2021 in PCT/JP2021/011783 filed Mar. 22, 2021, 2 pages.

* cited by examiner

*Primary Examiner* — Sahana S Kaup
*Assistant Examiner* — Ashlee E Wertz
(74) *Attorney, Agent, or Firm* — Oblon, McClelland, Maier & Neustadt, L.L.P.

(57) ABSTRACT

A composition for external preparation for skin including the following components (A), (B), and (C). (A) includes from 1 to 30 mass % of a polymer having a silicone moiety in which a ratio of deformation is 0.3 or more and 1 or less, and in a bend resistance test using a cylindrical mandrel method a minimum diameter of a cylindrical mandrel which causes no cracks in a polymer film is 2 mm or longer and 25 mm or shorter. (B) includes a volatile oil having a volatilization rate of 14% or more after drying at 1 atmosphere, at 40° C., and an R.H. of 60% for 30 minutes. (C) includes a polyol and a mass ratio of the component (A) to the component (C), (A)/(C), is from 3 to 200.

7 Claims, 1 Drawing Sheet

TOPICAL SKIN PREPARATION COMPOSITION

CROSS REFERENCE TO RELATED APPLICATIONS

This application is a National Stage entry under 35 U.S.C. § 371 of PCT/JP2021/011783, filed on Mar. 22, 2021, and claims priority to Japanese Patent Application No. 2020-066247, filed on Apr. 1, 2020. The entire contents of both are incorporated herein by reference.

FIELD OF THE INVENTION

The present invention relates to a composition for external preparation for skin.

BACKGROUND OF THE INVENTION

Human skin has more wrinkles with aging. This is part of an aging phenomenon of the skin and depends on multiple factors such as change in skin tissues and effect of exposure to an ultraviolet ray.

Conventionally, skin care products and the like for making skin wrinkles less noticeable have been studied. However, these products have an extremely low improving effect and have failed to gain satisfaction from women who have trouble of wrinkles.

Meanwhile, cosmetics compounded with a film-forming polymer are known which are intended to improve the uniformity of a makeup film and the makeup lasting quality. For example, Patent Literature 1 describes that a cosmetic containing a film-forming polymer in which a predetermined functional group is introduced into the skeleton of a polycycloolefin polymer allows makeup to last and achieves a favorable feel.

(Patent Literature 1): JP-A-2012-17317

SUMMARY OF THE INVENTION

The present invention relates to a composition for external preparation for skin comprising the following components (A), (B), and (C):

(A) from 1 to 30 mass % of a polymer having a silicone moiety in which a ratio of deformation measured by the following method (1) is 0.3 or more and 1 or less, and a minimum diameter of a cylindrical mandrel which causes no cracks in a film of the polymer measured by the bend resistance test using a cylindrical mandrel method performed by the following method (2) is 2 mm or longer and 25 mm or shorter:

Method (1): A 10 mass % hexamethyldisiloxane solution of the polymer is prepared. 0.005 g of the solution is applied to an area of 20 mm width×50 mm length on one side of a polyethylene sheet of 20 mm width×100 mm length×0.03 mm thickness in the length direction from one end of a short side, and the polyethylene sheet is dried in a thermostatic oven set at 40° C. for 10 minutes. Assuming the length of the polyethylene sheet portion coated with the solution as L1 and the length of a polyethylene sheet portion deformed by shrinkage after drying as L2, the value of L2/L1 is defined as ratio of deformation;

Method (2): A 30 mass % hexamethyldisiloxane solution of the polymer is prepared. The solution is applied to a polyethylene terephthalate film of 50 mm width×100 mm length×0.1 mm thickness using a 200 km applicator, and the film is dried in a thermostatic oven set at 40° C. for 120 minutes to prepare a test piece. A bend resistance test is performed using the test piece in accordance with a cylindrical mandrel method defined in JIS K5600-5-1:1999 to obtain the minimum diameter of a cylindrical mandrel which causes no cracks in the polymer film on the test piece, (B) a volatile oil having a volatilization rate of 14% or more after drying at 1 atmosphere, 40° C., and R.H. of 60% for 30 minutes, and (C) a polyol, wherein the mass ratio of the component (A) to the component (C), (A)/(C), is from 3 to 200.

DETAILED DESCRIPTION OF THE INVENTION

Conventional cosmetics comprising a film-forming polymer have had such problems that their wrinkle-reducing effect is insufficient, and the unevenness in the thickness of the coating film and cloudiness during drying stand out.

The present inventors found that, by using a polyol in a specific film-forming polymer in a specific proportion, a composition for external preparation for skin can be obtained which maintains high shrinkage to improve skin wrinkles, has no unevenness in the thickness of the coating film, and prevents cloudiness after coating and during drying, and accomplished the present invention.

The composition for external preparation for skin of the present invention can improve skin wrinkles, has no unevenness in the thickness of the coating film, and prevents cloudiness after coating and during drying.

In the present specification, the term "skin wrinkles" means roughness or folds that occur on the skin surface, which are changes in the shape that occur because of sagging of the skin. Skin wrinkles are likely to occur around the mouth and the eyes, on the forehead, the neck, and the body, and the like. Small folds are fine wrinkles, and large folds are large wrinkles, which occur with a flow of enlarged skin pores of nasolabial folds, cheek folds, and the like. The composition for external preparation for skin of the present invention exhibits an effect of making both types of wrinkles less noticeable and can improve even large wrinkles, such as nasolabial folds, in particular, in a noninvasive manner.

<Component (A)>

The component (A) used in the present invention is a polymer having a silicone moiety in which a ratio of deformation measured by the method (1) is 0.3 or more and 1 or less, and in a bend resistance test using a cylindrical mandrel method performed by the method (2), the minimum diameter of a cylindrical mandrel which causes no cracks in the polymer is 2 mm or longer and 25 mm or shorter.

When the component (A) satisfies the above-mentioned ratio of deformation measured by the method (1), for example, a composition comprising a polymer which is the component (A) is used by applying it to the skin surrounding wrinkles by application or the like, and then when the composition is dried, shrinkage of the film comprising the polymer as well as the skin surface attached to the film occurs. Because the skin portion with wrinkles is stretched by this action, wrinkles can be made less noticeable.

Figure 1:
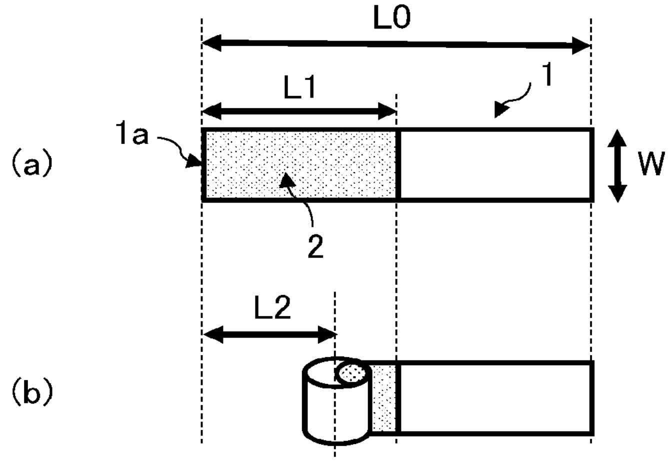
FIG. 1 is a diagram explaining a method for assessing the ratio of deformation (L2/L1) of a polymer by the method (1)

The method for assessing the ratio of deformation (L2/L1) of the component (A) by the method (1) is explained below with reference to FIG. 1. First, a 10 mass % hexamethyldisiloxane solution of the component (A) used for the composition is prepared. 0.005 g of this solution is applied to an area of 20 mm width×50 mm length (a portion of 2 shown in FIG. 1 (*a*)) on one side of a polyethylene sheet 1 of 20 mm width (W)×100 mm length (L0)×0.03 mm thickness shown in FIG. 1 (*a*) in the length direction from one end 1*a* of a short side of the polyethylene sheet 1, and the polyethylene sheet is dried in a thermostatic oven set at 40° C. for 10 minutes. FIG. 1 (*b*) is a schematic view showing that the polyethylene sheet 1 coated with the solution was dried, and then a portion thereof was deformed (curled) by shrinkage of the polymer which was the component (A).

Assuming the length of the polyethylene sheet portion coated with the solution as L1 (50 mm) and the length of the polyethylene sheet portion deformed by shrinkage after drying in the dried polyethylene sheet (FIG. 1 (*b*)) as L2, L2/L1 is calculated, and the value is defined as ratio of deformation. L2 is defined as the mean value of lengths calculated for two long sides of the polyethylene sheet. A larger L2/L1 value means a greater degree of polymer shrinkage due to dryness, and the upper limit of L2/L1 is 1.

In view of smoothing skin wrinkles to make them less noticeable, the ratio of deformation, L2/L1, of the component (A) assessed by the method (1) is 0.3 or more, preferably 0.5 or more, more preferably 0.6 or more, even more preferably 0.7 or more, even more preferably 0.8 or more, even more preferably 0.85 or more, even more preferably 0.9 or more, even more preferably 0.95 or more, and the upper limit thereof is 1.

Specifically, the ratio of deformation can be assessed by the methods described in the examples.

Further, the component (A) has excellent bend resistance, and in a bend resistance test using a cylindrical mandrel method performed by the method (2), the minimum diameter of the cylindrical mandrel which causes no cracks in a film of a polymer which is the component (A) is 2 mm or longer and 25 mm or shorter. With this diameter, a film formed by a composition comprising the component (A) is unlikely to crack and likely to shrink while following the skin shape.

A smaller minimum diameter of the cylindrical mandrel means more favorable bend resistance. In view of achieving sufficient adhesiveness between a film comprising the polymer and the skin surface during shrinkage of the film, the minimum diameter is 25 mm or shorter, preferably 20 mm or shorter, more preferably 12 mm or shorter, even more preferably 8 mm or shorter, even more preferably 6 mm or shorter, even more preferably 5 mm or shorter. Meanwhile, in view of imparting sufficient strength and a shape controlling effect to smooth skin wrinkles and make them less noticeable, the minimum diameter of the cylindrical mandrel which causes no cracks is 2 mm or longer, preferably 3 mm or longer. The specific range of the minimum diameter of the cylindrical mandrel is from 2 to 25 mm, preferably from 2 to 20 mm, more preferably from 2 to 12 mm, even more preferably from 2 to 8 mm, even more preferably from 3 to 6 mm, even more preferably from 3 to 5 mm.

The bend resistance can be assessed using a type 1 bend tester defined in JIS K5600-5-1:1999, specifically by the methods described in the examples.

Further, for the component (A), the ratio of the ratio of deformation obtained by the method (1) to the minimum diameter (mm) of the mandrel obtained by the method (2) [(ratio of deformation)/(minimum diameter of the mandrel)] is preferably 0.01 or more, more preferably 0.02 or more, even more preferably 0.10 or more, even more preferably 0.15 or more in view of a skin wrinkle-reducing effect; and is preferably 0.5 or less, more preferably 0.4 or less in view of imparting strength and the shape controlling effect sufficient to smooth skin wrinkles and make them less noticeable. A specific range of the ratio is preferably from 0.01 to 0.5, more preferably from 0.02 to 0.5, even more preferably from 0.10 to 0.5, even more preferably from 0.15 to 0.5, even more preferably from 0.15 to 0.4.

In the present invention, the term "silicone moiety" refers to a structure of the following formula (I):

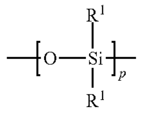

(I)

In the formula (I), $R^1$ is each independently a hydrocarbon group having one or more and 12 or less carbon atoms, and p is an integer of 1 or more. In view of smoothing skin wrinkles to make them less noticeable and achieving a sufficient wrinkle-reducing effect (hereinafter, also referred to as "skin wrinkle-reducing effect") and in view of versatility when used, $R^1$ is preferably an alkyl group having one or more and 12 or less carbon atoms or an aryl group having six or more and 12 or less carbon atoms, more preferably an alkyl group or a phenyl group having one or more and 12 or less carbon atoms, even more preferably an alkyl group having one or more and three or less carbon atoms, even more preferably methyl group.

It is sufficient that the polymer which is the component (A) has a silicone moiety, and the polymer may be a polymer consisting of a silicone moiety alone. In view of preparing a polymer having the predetermined characteristics, however, a polymer having a silicone moiety as a part thereof is preferred. The polymer may comprise not only a D unit ($R^1_2SiO_{2/2}$) structure, but also an M unit ($R^1_3SiO_{1/2}$) structure, a T unit ($R^1SiO_{3/2}$) structure, and a Q unit ($SiO_{4/2}$) structure.

When a polymer has a silicone moiety as a part thereof, the silicone moiety may exist in either the main chain or a side chain of the polymer and preferably exists in a side chain in view of preparing a polymer having the predetermined characteristics.

When the silicone moiety exists in the main chain of a polymer, the binding form is not particularly limited, and for example, the silicone moiety may exist at the end of the main chain of the polymer, or the polymer may be a copolymer in which the silicone moiety binds to the main chain of a polymer in a block or at random. Further, a graft-modified polymer with a compound having a silicone moiety can be used.

The component (A) used in the present invention is preferably a silicone-modified polymer, and specific examples thereof include silicone-modified polymers containing norbornane moiety, such as silicone-modified polynorbornenes; silicone-modified Pullulans; silicic acid compounds having a silicone moiety, such as trialkylsiloxysilicic acid, fluorine-modified alkylsiloxysilicic acid, and phenyl-modified alkylsiloxysilicic acid; and silicone dendrimers.

(Silicone-Modified Polymers Containing a Norbornane Moiety)

In the present invention, a norbornane moiety means a structure of the following formula. It is sufficient that the silicone-modified polymer containing a norbornane moiety is a silicone-modified polymer having the structure of the following formula at an arbitrary site in the polymer.

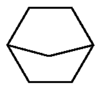

Examples of silicone-modified polymers containing a norbornane moiety include polymers having a repeating unit of the following formula (1) or (2):

(1)

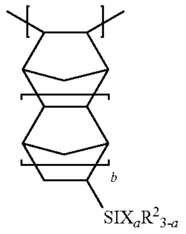

wherein $R^2$ is each independently an alkyl group having one or more and 12 or less carbon atoms, X is a group of the following formula (i). a is an integer of 1 or more and 3 or less, and b is an integer of 0 or more and 2 or less.

(i)

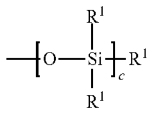

wherein $R^1$ is the same as described above, and c is an integer of 1 or more and 5 or less.

(2)

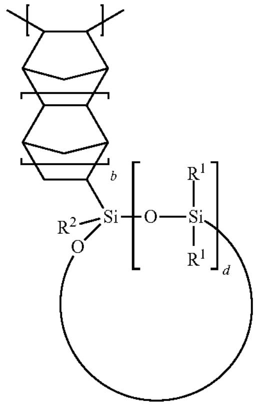

wherein $R^1$, $R^2$, and b are the same as described above, and d is an integer of 2 or more and 5 or less.

In the formula (1), $R^2$ is each independently an alkyl group having one or more and 12 or less carbon atoms, and in view of the skin wrinkle-reducing effect and in view of versatility, $R^2$ is preferably methyl group, ethyl group, n-propyl group, butyl group, or pentyl group, more preferably methyl group.

X is a group of the formula (i). In the formula (i), $R^1$ is each independently a hydrocarbon group having one or more and 12 or less carbon atoms. In view of the skin wrinkle-reducing effect and in view of versatility, $R^1$ is preferably an alkyl group having one or more and 12 or less carbon atoms or an aryl group having six or more and 12 or less carbon atoms, more preferably an alkyl group or a phenyl group having one or more and 12 or less carbon atoms, even more preferably an alkyl group having one or more and three or less carbon atoms, even more preferably methyl group. c is an integer of 1 or more and 5 or less, and in view of versatility, c is preferably equal to 1. Specifically, X is preferably a trimethylsiloxy group.

a is an integer of 1 or more and 3 or less, and the polymer may be, for example, a polymer having a mixture of a repeating unit with a being 2 and a repeating unit with a being 3. In view of versatility, a is preferably 3. b is an integer of 0 or more and 2 or less, and in the same view, b is preferably 0, 1, or a combination thereof, more preferably 0.

In the formula (2), $R^1$, $R^2$, and b are the same as described above. d is an integer of 2 or more and 5 or less, and in view of versatility, d is preferably equal to 2. In the cyclic silicone moiety in the formula (2), it is preferred in the same view that $R^1$ and $R^2$ are methyl group, and that d is 2 or 3. Specifically, the cyclic silicone moiety in the formula (2) is preferably a structure of the following formula (4) or (5):

(4)

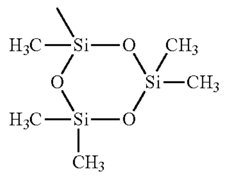

(5)

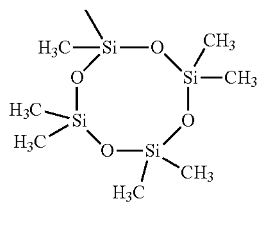

In view of the skin wrinkle-reducing effect, the proportion of repeating units of the formula (1) or (2) in a silicone-modified polymer containing a norbornane moiety is preferably 10% or more, more preferably 30% or more, even more preferably 50% or more of the number of all repeating units in the polymer. The upper limit is 100%, and the proportion is preferably 95% or less, more preferably 90% or less, even more preferably 70% or less. In a silicone-modified polymer containing a norbornane moiety, the specific range of the number of repeating units of the formula (1) or (2) is preferably from 10% to 100%, more preferably from 10% to 95%, even more preferably from 30% to 90%, even more preferably from 50% to 70% of the number of all repeating units in the polymer.

A silicone-modified polymer containing a norbornane moiety may have a repeating unit of the following formula (3) in addition to the repeating unit of the formula (1) or (2).

(3)

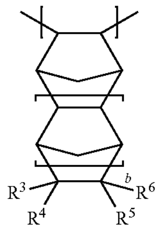

wherein $R^3$ to $R^6$ are each independently a substituent group selected from the group consisting of a hydrogen atom; a halogen atom; an alkyl group, an alkenyl group, a cycloalkyl group, an aryl group, an alkoxy group, an aryloxy group, and a halogenated hydrocarbon group which have one or more and 10 or less carbon atoms; an oxetanyl group; an alkoxycarbonyl group; a polyoxyalkylene group; a polyglyceryl group; and an alkoxysilyl group. Two groups chosen from $R^3$ to $R^6$ may be taken together to form an aliphatic ring structure, an aromatic ring structure, a carboimide group, or an acid anhydride group. b is the same as described above.

In view of the skin wrinkle-reducing effect, the proportion of the above-described repeating units of the formula (3) in a silicone-modified polymer containing a norbornane moiety is preferably 90% or less, more preferably 70% or less, even more preferably 50% or less of the number of all repeating units in the polymer. Further, when the above-described repeating units of the formula (3) are contained, the proportion thereof is preferably 5% or more, more preferably 10% or more, even more preferably 30% or more of the number of all repeating units in the polymer. In a silicone-modified polymer containing a norbornane moiety, the specific range of the number of repeating units of the formula (3) is preferably from 5% to 90%, more preferably from 10% to 70%, even more preferably from 30% to 50% of the number of all repeating units in the polymer.

The proportion of the above-described repeating units of the formulas (1) to (3) in a silicone-modified polymer containing a norbornane moiety can be obtained by $^1$H-NMR measurement.

The silicone-modified polymer containing a norbornane moiety is preferably a silicone-modified polynorbornene, more preferably a silicone-modified polynorbornene of the following formula (6):

(6)

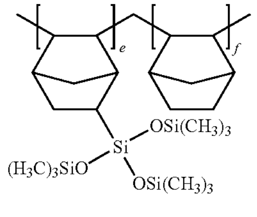

wherein e and f are the number of repeating units and are each independently an integer of 1 or more.

In view of the skin wrinkle-reducing effect, the ratio of e and f, e/f, in the formula (6) is preferably from 20/80 to 90/10 (mol/mol), more preferably from 30/70 to 80/20 (mol/mol), even more preferably from 50/50 to 70/30 (mol/mol).

In view of balancing shrinkage and bend resistance and in view of the skin wrinkle-reducing effect, the number average molecular weight (Mn) of a silicone-modified polymer containing a norbornane moiety is preferably 50,000 or more, more preferably 100,000 or more, even more preferably 200,000 or more, and preferably 2,000,000 or less, more preferably 1,500,000 or less, even more preferably 800,000 or less, even more preferably 600,000 or less. The specific range of the number average molecular weight (Mn) of a silicone-modified polymer containing a norbornane moiety is preferably from 50,000 to 2,000,000, more preferably from 100,000 to 1,500,000, even more preferably from 200,000 to 800,000, even more preferably from 200,000 to 600,000.

The number average molecular weight (Mn) of the polymer can be measured by gel filtration chromatography (GPC) using polystyrene as a reference substance, and specifically by the methods described in the examples.

The silicone-modified polymer containing a norbornane moiety can be obtained by, for example, a known method of addition polymerization of a silicone-modified cyclic olefin monomer which comprises a norbornane structure or can form a norbornane structure.

For example, the above-described silicone-modified polymer containing a norbornane moiety having the repeating unit of the formula (1) or (2) can be obtained by addition polymerization of a cyclic olefin monomer of the following formula (1a) or (2a). Further, a cyclic olefin monomer of the formula (3a) may be copolymerized.

(1a)

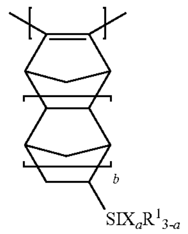

wherein $R^1$ is each independently an alkyl group having one or more and 12 or less carbon atoms, and X is a group of the following formula (i). a is an integer of 1 or more and 3 or less, and b is an integer of 0 or more and 2 or less.

(i)

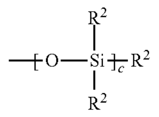

wherein $R^2$ is each independently a hydrocarbon group having one or more and 12 or less carbon atoms, and c is an integer of 1 or more and 5 or less.

(2a)

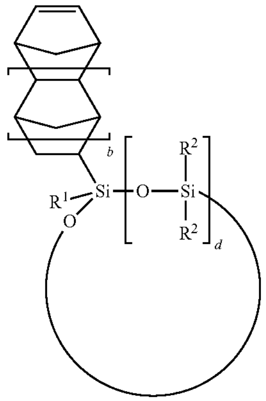

wherein $R^1$, $R^2$, and b are the same as described above, and d is an integer of 2 or more and 5 or less.

(3a)

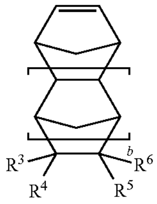

wherein $R^3$ to $R^6$ are each independently a substituent group selected from the group consisting of a hydrogen atom; a halogen atom; an alkyl group, an alkenyl group, a cycloalkyl group, an aryl group, an alkoxy group, an aryloxy group, and a halogenated hydrocarbon group which have one or more and 10 or less carbon atoms; an oxetanyl group; an alkoxycarbonyl group; a polyoxyalkylene group; a polyglyceryl group; and an alkoxysilyl group. Two groups chosen from $R^3$ to $R^6$ may be taken together to form an aliphatic ring structure, an aromatic ring structure, a carboimide group, or an acid anhydride group. b is the same as described above.

When the above-described cyclic olefin monomer of the formula (3a) is copolymerized, the use amount thereof is, in view of the skin wrinkle-reducing effect, preferably 90 mol % or less, more preferably 70 mol % or less, even more preferably 50 mol % or less, and preferably 5 mol % or more, more preferably 10 mol % or more, even more preferably 30 mol % or more, assuming the amount of all monomers used for polymerization as 100 mol %.

The above-described silicone-modified polynorbornene of the formula (6) can be obtained by addition polymerization of tris(trimethylsiloxy)silylnorbornene of the following formula (6a) and norbornene:

(6a)

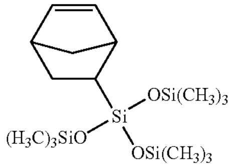

In view of the skin wrinkle-reducing effect, the copolymerization ratio of tris(trimethylsiloxy)silylnorbornene and norbornene is preferably from 20/80 to 90/10 (mol/mol), more preferably from 30/70 to 80/20 (mol/mol), even more preferably from 50/50 to 70/30 (mol/mol).

Of note, all the repeating units of the formulas (1) to (3) and (6) represent a unit of a 2,3-addition structure of a cyclic olefin monomer as a raw material monomer and may contain a unit of a 2,7-addition structure obtained by addition polymerization of the cyclic olefin monomer.

The silicone-modified polymer containing a norbornane moiety is preferably a (norbornene/tris(trimethylsiloxy)silylnorbornene) copolymer, i.e., a compound which is expressed as NORBORNENE/TRIS(TRIMETHYLSILOXY)SILYLNORBORNENE COPOLYMER, as the INCI name (International Cosmetic Ingredient Dictionary and Handbook, 16th Edition, Volume 2, 2016, p. 2274).

Examples of commercially available silicone-modified polymers containing a norbornane moiety include "NBN-30-ID" (an isododecane solution of a norbornene/tris(trimethylsiloxy)silylnorbornene) copolymer) manufactured by Shin-Etsu Chemical Co., Ltd.

(Silicone-Modified Pullulans)

Examples of silicone-modified Pullulans include Pullulans having a silicone moiety in a side chain. Specifically, in view of the skin wrinkle-reducing effect and in view of versatility, a silicone-modified Pullulan in which at least some hydrogen atoms of an OH group in the Pullulan is substituted with a group of the following formula (7) is preferred:

$$—Z^1—SiX_aR^2_{3-a} \quad (7)$$

wherein $Z^1$ is a single bond or divalent organic group. $R^2$, X, and a are the same as described above, and in the same view, X is preferably trimethylsiloxy group, and a is preferably 3.

In the same view, in the formula (7), $Z^1$ is preferably a divalent organic group, more preferably a divalent group of the following formula (8) or (9), even more preferably a divalent group of the following formula (9).

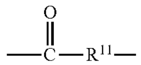

(8)

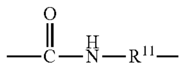

(9)

wherein $R^{11}$ is an alkylene group having one or more and 10 or less carbon atoms, and examples thereof include methylene group, ethylene group, trimethylene group, propylene group, and butylene group. Of these, in the same view, ethylene group, trimethylene group, and propylene group are preferred, and trimethylene group and propylene group are more preferred.

Examples of commercially available silicone-modified Pullulans include "TSPL-30-ID" (an isododecane solution of tri(trimethylsiloxy)silyl propyl carbamide acid Pullulan) and "TSPL-30-D5" (a cyclopentasiloxane solution of tri(trimethylsiloxy)silyl propyl carbamide acid Pullulan), which are manufactured by Shin-Etsu Chemical Co., Ltd.

(Silicic Acid Compounds Having a Silicone Moiety)

Examples of the silicic acid compound having a silicone moiety used in the present invention include silicate compounds having a silicone moiety at an end thereof, and examples thereof include trialkylsiloxysilicic acids, fluorine-modified alkylsiloxysilicic acids, and phenyl-modified alkylsiloxysilicic acids.

In view of the skin wrinkle-reducing effect and in view of versatility, an alkyl group in a trialkylsiloxysilicic acid has preferably one or more and 10 or less carbon atoms, more preferably one or more and four or less carbon atoms, and is even more preferably methyl group. Specific examples of trialkylsiloxysilicic acids include trimethylsiloxysilicic acid.

Examples of fluorine-modified alkylsiloxysilicic acids include compounds in which at least some hydrogen atoms in an alkyl group in a trialkylsiloxysilicic acid are substituted with a fluorine atom. Specific examples thereof include trifluoropropyldimethylsiloxysilicic acid and trifluoropropyldimethyl/trimethylsiloxysilicic acid.

Examples of phenyl-modified alkylsiloxysilicic acids include phenylpropyldimethylsiloxysilicic acid and phenylpropyldimethyl/trimethylsiloxysilicic acid.

In view of the skin wrinkle-reducing effect, one or more selected from the group consisting of trialkylsiloxysilicic acids and fluorine-modified alkylsiloxysilicic acids are preferred among the silicic acid compounds having a silicone moiety.

Examples of commercially available silicic acid compounds having a silicone moiety include trimethylsiloxysilicic acids (solution), such as "KF-7312J," "KF-7312K," "KF-7312T," "KF-7312L," "X-21-5249," "X-21-5250," "KF-9021," "X-21-5595," "X-21-5616," "KF-9021L," "X-21-5249L," and "X-21-5250L," which are manufactured by Shin-Etsu Chemical Co., Ltd., and "XS66-B8226" (a cyclopentasiloxane solution of trifluoropropyldimethyl/trimethylsiloxysilicic acid), "XS66-B8636" (a dimethicone solution of trifluoropropyldimethyl/trimethylsiloxysilicic acid), and "SilShine 151" (phenylpropyldimethylsiloxysilicic acid), which are manufactured by Momentive Performance Materials Japan LLC.

(Silicone Dendrimers)

Examples of silicone dendrimers include vinyl polymers having a siloxane dendrimer structure in a side chain thereof. Specifically, in view of the skin wrinkle-reducing effect and in view of versatility, the siloxane dendrimer structure is preferably a group of the following formula (10):

(10)

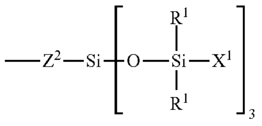

wherein $R^1$ is the same as described above. $Z^2$ is a single bond or divalent organic group. $X^1$ is a group of the following formula (11) when i is equal to 1, and i is an integer of 1 or more and 10 or less, indicating the hierarchy of the group:

(11)

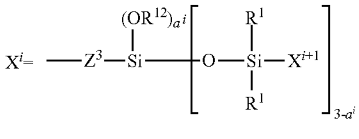

wherein $R^1$ is the same as described above, and $R^{12}$ is an alkyl group having one or more and 10 or less carbon atoms. $Z^3$ is an alkylene group having two or more and 10 or less carbon atoms. $X^{i+1}$ is a hydrogen atom, an alkyl group having one or more and 10 or less carbon atoms, an aryl group, or a group of the formula (11), and $a^i$ is an integer of 0 or more and 3 or less.

In the formula (10), $Z^2$ is a single bond or divalent organic group, in view of versatility, preferably a divalent organic group, more preferably a divalent group of the following formula (12), (13), or (14):

(12)

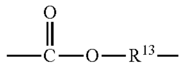

(13)

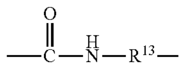

(14)

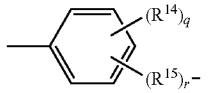

wherein $R^{13}$ is an alkylene group having one or more and 10 or less carbon atoms, and examples thereof include methylene group, ethylene group, trimethylene group, propylene group, and butylene group. In view of versatility, ethylene group, trimethylene group, and propylene group are preferred. $R^{14}$ is an alkyl group having one or more and 10 or less carbon atoms, and examples thereof include methyl group, ethyl group, propyl group, and butyl group. In the same view, methyl group is preferred. $R^{15}$ is an alkylene group having one or more and 10 or less carbon atoms, and examples thereof include methylene group, ethylene group, trimethylene group, propylene group, and butylene group. In the same view, ethylene group is preferred. q is an integer of 0 or more and 4 or less, and r is 0 or 1.

Examples of vinyl polymers having the above-described siloxane dendrimer structure in a side chain (hereinafter, also referred to simply as "vinyl polymer") include polymers having a repeating unit derived from a monomer of the following formula (15):

(15)

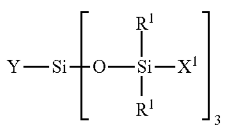

wherein $R^1$ and $X^1$ are the same as described above. Y is a group comprising a vinyl bond, and examples thereof include vinyl group, 2-acryloyloxyethyl group, 3-acryloyloxypropyl group, 2-methacryloyloxyethyl group, 3-methacryloyloxypropyl group, 4-vinylphenyl group, 3-vinylphenyl group, 4-(2-propenyl)phenyl group, 3-(2-propenyl)phenyl group, 2-(4-vinylphenyl)ethyl group, 2-(3-vinylphenyl)ethyl group, allyl group, and 5-hexenyl group. Of these, in view of versatility, (meth)acryloyl group and vinyl group are preferred, and (meth)acryloyl group is more preferred.

The vinyl polymer may further comprise a repeating unit derived from a vinyl monomer other than the monomer of the formula (15). Examples of such vinyl monomers include monomers which have a group comprising a vinyl bond and are not the monomer of the formula (15), and examples thereof include (meth)acrylic acid, alkyl(meth)acrylate, hydroxyalkyl(meth)acrylate, aromatic ring-comprising (meth)acrylate, fatty acid vinyl esters, (meth)acrylamide, styrene, and derivatives thereof. One or more of these can be used. Of these, (meth)acryl monomers, such as (meth) acrylic acid, alkyl(meth)acrylate, hydroxyalkyl(meth)acrylate, and aromatic ring-comprising (meth)acrylate, are preferred in view of versatility.

In view of the skin wrinkle-reducing effect, the content of a repeating unit derived from the monomer of the formula (15) in a vinyl polymer is preferably 0.1 mass % or more, more preferably 10 mass % or more, even more preferably 20 mass % or more of all repeating units in the vinyl polymer. The upper limit is 100 mass %.

The vinyl polymer is more preferably an acrylic polymer. Specifically, preferred examples of silicone dendrimers include an acrylic polymer having a siloxane dendrimer structure in a side chain (hereinafter, also referred to as "acryl silicone dendrimer"). An acryl silicone dendrimer is a polymer having a repeating unit derived from a monomer in which Y is a (meth)acroyl group in the formula (15) and may further comprise a repeating unit derived from a (meth)acrylic monomer other than the monomer of formula (15).

Examples of commercially available silicone dendrimers include acrylic silicone dendrimers, such as "FA 4001 CM Silicone Acrylate" (a cyclopentasiloxane solution of acrylate-polytrimethylsiloxymethacrylate copolymer) and "FA 4002 ID Silicone Acrylate" (an isododecane solution of acrylate-polytrimethylsiloxymethacrylate copolymer), which are manufactured by Dow Corning Toray Co., Ltd.

In view of the skin wrinkle-reducing effect, among the above-mentioned polymers, the component (A) is preferably one or more selected from the group consisting of silicone-modified polynorbornenes, silicone-modified Pullulans, trimethylsiloxysilicic acid, trifluoropropyldimethyl/trimethylsiloxysilicic acid, and acrylic silicone dendrimers, more preferably one or more selected from the group consisting of silicone-modified polynorbornenes, silicone-modified Pullulans, trimethylsiloxysilicic acid, and trifluoropropyldimethyl/trimethylsiloxysilicic acid. In view of the skin wrinkle-reducing effect and in view of bend resistance, one or more selected from the group consisting of silicone-modified polynorbornenes and silicone-modified Pullulans are even preferred, and silicone-modified polynorbornenes are even more preferred.

One or more different components (A) can be used in combination, and in view of the skin wrinkle-reducing effect, the solid content thereof in the whole composition is 1 mass % or more, preferably 2 mass % or more, more preferably 4 mass % or more, even more preferably 5 mass % or more, and is 30 mass % or less, preferably 25 mass % or less, more preferably 20 mass % or less, even more preferably 18 mass % or less. Further, the solid content of the component (A) in the whole composition is from 1 to 30 mass %, preferably from 2 to 25 mass %, more preferably from 4 to 20 mass %, even more preferably from 5 to 18 mass %.

<Component (B)>

The component (B) used in the present invention is a volatile oil with a volatilization rate of 14% or more after drying at 1 atmosphere, 40° C., and R.H. of 60% for 30 minutes. Since the drying speed of a composition comprising the component (A) is improved when the component (B) is added, shrinkage of the component (A) is accelerated during the drying process, leading to improvement in the effect of smoothing skin wrinkles to make them less noticeable.

In view of obtaining the above-described effects, the volatilization rate of the component (B) after drying at 1 atmosphere, 40° C., and R.H. of 60% for 30 minutes is preferably 18% or more, more preferably 25% or more, even more preferably 30% or more, even more preferably 45% or more, even more preferably 65% or more, even more preferably 80% or more, even more preferably 95% or more. The upper limit is 100%.

After placing 0.5 g of a sample in a glass petri dish of 40 mm in diameter and leaving and drying it in an environment of 1 atmosphere, R.H. of 60%, and 40° C. for 30 minutes, the volatilization rate of the component (B) is obtained as a value of $\{(W_0-W_1)/W_0\}\times 100$ assuming the sample mass before drying as $W_0$ (g) and the sample mass after drying as $W_1$ (g). A greater value means a faster volatilization speed, resulting in easily getting dry.

Of note, two or more different volatile oils may be used as the component (B).

The above-described volatilization rate can be specifically measured by the methods described in the examples.

In view of increasing the skin wrinkle-reducing effect, examples of the component (B) include one or more oil solutions selected from the group consisting of hydrocarbon oils and silicone oils which have a volatilization rate within the above-mentioned range. Of these, one or more selected from the group consisting of isododecane (volatilization rate, 33%), hexamethyldisiloxane (volatilization rate, 100%), methyl trimethicone, and dimethylpolysiloxane having kinematic viscosity of 2 cSt or less at 25° C. are preferred, and one or more selected from the group consisting of isododecane, hexamethyldisiloxane, methyl trimethicone, and octamethyldimethylpolysiloxane are more preferred. Of note, the kinematic viscosity can be measured by, for example, using an Ubbelohde's viscometer.

In view of increasing the skin wrinkle-reducing effect, the component (B) is more preferably one or more selected from the group consisting of isododecane, hexamethyldisiloxane, and polydimethylsiloxane having kinematic viscosity of 1.5 cSt or less at 25° C., even more preferably one or more selected from the group consisting of hexamethyldisiloxane and polydimethylsiloxane having kinematic viscosity of 1 cSt or less at 25° C., even more preferably hexamethyldisiloxane.

Examples of commercially available hexamethyldisiloxane and polydimethylsiloxane having kinematic viscosity of 2 cSt or less at 25° C. include "KF-96L-0.65cs" (hexamethyldisiloxane), "TMF1.5," "KF-96L-1cs" (octamethyltrisiloxane), "KF-96L-1.5cs," and "KF-96L-2cs," which are manufactured by Shin-Etsu Chemical Co., Ltd., "SH200C Fluid 1cs" and "SH200C Fluid 1.5cs," which are manufactured by Dow Corning Toray Co., Ltd., "TSF451-0.65" manufactured by Momentive Performance Materials Japan LLC, and "BELSIL DM0.65" manufactured by Wacker Asahikasei Silicone Co., Ltd.

One or more different components (B) can be used in combination. In view of increasing the skin wrinkle-reducing effect, the content thereof is preferably 1 mass % or more, more preferably 30 mass % or more, even more preferably 50 mass % or more, even more preferably 70 mass % or more, even more preferably 72 mass % or more, and preferably 98 mass % or less, more preferably 97 mass % or less, even more preferably 94 mass % or less, even more preferably 92 mass % or less, even more preferably 90 mass % or less in the whole composition. Further, the content of the component (B) is preferably from 1 to 98 mass %, more preferably from 30 to 97 mass %, even more preferably from 50 to 94 mass %, even more preferably from 70 to 92 mass %, even more preferably from 72 to 90 mass % in the whole composition.

In the present invention, in view of the skin wrinkle-reducing effect, the mass ratio of the component (A) to the component (B), (A)/(B), is preferably 0.02 or more, more preferably 0.03 or more, even more preferably 0.04 or more, even more preferably 0.05 or more, even more preferably 0.1 or more and preferably 1 or less, more preferably 0.7 or less, even more preferably 0.4 or less, even more preferably 0.25 or less. Further, the mass ratio of the component (A) to the component (B), (A)/(B), is preferably from 0.02 to 1, more preferably from 0.03 to 0.7, even more preferably from 0.04 to 0.4, even more preferably from 0.05 to 0.25, even more preferably from 0.1 to 0.25.

<Component (C)>

The polyol which is the component (C) used in the present invention is a compound having two or more hydroxyl groups in a molecule, and any polyols can be used as long as they are used for usual agents for skin external use.

Examples of dihydric alcohols include ethylene glycol, diethylene glycol, triethylene glycol, polyethylene glycol, propylene glycol, dipropylene glycol, tripropylene glycol, polypropylene glycol, butylene glycol, and propanediol. Examples of trihydric alcohols include glycerin and trimethylol propane. Examples of tetrahydric alcohols include diglycerin and erythritol. Examples of pentahydric or more polyhydric alcohols include polyglycerins such as triglycerin; and sugars and sugar alcohols such as glucose, maltose, maltitol, sucrose, xylitol, sorbitol, mannitol, polyoxyethylene methyl glucoside, polyoxyethylene ethyl glucoside, and polyoxyethylene propylene glucoside.

In view of achieving a uniform, nice-looking, natural finish having no uneven thickness and preventing cloudiness, the component (C) is preferably one or more selected from the group consisting of glycols, glycerins, and saccharides, and more preferably comprises at least one or more selected from the group consisting of propylene glycol, butylene glycol, glycerin, polypropylene glycol, and sorbitol.

One or more different components (C) can be used in combination, and in view of achieving a uniform, nice-looking, natural finish having no uneven thickness and preventing cloudiness, the content of the components (C) is preferably 0.1 mass % or more, more preferably 0.2 mass % or more, even more preferably 0.3 mass % or more, even more preferably 0.4 mass % or more, and preferably 20 mass % or less, more preferably 10 mass % or less, even more preferably 6 mass % or less, even more preferably 4.5 mass % or less in the whole composition. Further, the content of the component (C) is preferably 0.1 to 20 mass %, more preferably 0.2 to 10 mass %, even more preferably 0.3 to 6 mass %, even more preferably 0.4 to 4.5 mass % in the whole composition.

In the present invention, in view of improving wrinkles, having no unevenness in the thickness of the coating film, and preventing cloudiness after coating and during drying, the mass ratio of the component (A) to the component (C), (A)/(C), is 3 or more, preferably 4 or more, more preferably 5 or more, and 200 or less, preferably 100 or less, more preferably 50 or less, even more preferably 34 or less. Further, the mass ratio of the component (A) to the component (C), (A)/(C), is from 3 to 200, preferably from 3 to 100, more preferably from 4 to 50, even more preferably from 5 to 34.

<Component (D)>

The composition for external preparation for skin of the present invention can further comprise (D) a surfactant, and preferred examples thereof include anionic surfactants, cationic surfactants, nonionic surfactants, and ampholytic surfactants.

Surfactants of the component (D) are not limited as long as they are used for usual agents for skin external use, but they are preferably nonionic surfactants in view of being soluble in a volatile oil, preventing stickiness, and preventing the coating film from peeling and cloudiness over time.

Examples of nonionic surfactants include sorbitan fatty acid ester, glycerin fatty acid ester, polyglycerin fatty acid ester, propylene glycol fatty acid ester, polyethylene glycol fatty acid ester, sucrose fatty acid ester, polyoxyethylene fatty acid ester, polyoxyethylene sorbitan fatty acid ester, polyoxyethylenealkyl ether, polyoxyethylene sorbitol fatty acid ester, polyoxyethylene glycerin fatty acid ester, polyoxyethylene propylene glycol fatty acid ester, polyoxyethylene castor oil, polyoxyethylene hydrogenated castor oil, polyoxyethylene hydrogenated castor oils and fatty acid ester, polyoxyethylene phytostanol ether, polyoxyethylene phytosterose ether, polyoxyethylene cholestanol ether, polyoxyethylene cholesteryl ether, alkyl glyceryl ether-modified silicone, polyoxyalkylene-modified silicone, polyoxyalkylene-alkyl co-modified silicone, and polyoxyalkylene-fluoroalkyl co-modified silicone.

Of these, in view of increasing dispersibility/solubility of water and water-soluble components in an oil, a silicone surfactant is preferred, and a nonionic surfactant more preferably comprises one or more alkyl glyceryl ether-modified silicones and polyoxyalkylene-modified silicones, and more preferably polyoxyalkylene-modified silicones.

Examples of polyoxyalkylene-modified silicones which can be used include commercially available products such as SH3771M, SH3772M, SH3773M, SH3775M, SH3749, and DC5200, which are manufactured by Dow Corning Toray Co., Ltd, and KF-6011, KF-6012, KF-6013, KF-6015, KF-6016, KF6017, and KF-6004, which are manufactured by Shin-Etsu Chemical Co., Ltd.

In view of increasing dispersibility/solubility of water and water-soluble components in an oil, the HLB value of a nonionic surfactant is preferably 1 or more and 7 or less, more preferably 2 or more and 6 or less.

Here, HLB (Hydrophilic-Lypophilic Balance) represents the proportion of the molecular weight of a hydrophilic portion to the molecular weight of the whole surfactant and can be obtained by the Griffin's formula for nonionic surfactants.

The HLB value of a mixed surfactant composed of two or more nonionic surfactants is obtained as follows. The HLB of the mixed surfactant is obtained by calculating an arithmetic mean of the HLB values of each nonionic surfactant based on the mixing ratio.

$$\text{Mixed } HLB = \sum(HLBx \times Wx) \Big/ \sum Wx$$

HLBx represents the HLB value of a nonionic surfactant X.

Wx represents weight (g) of the nonionic surfactant X having the HLBx value.

One or more different nonionic surfactants can be used in combination, and in view of being soluble in a volatile oil and preventing stickiness, the content of the nonionic surfactants is preferably 30 mass % or less, more preferably 10 mass % or less, even more preferably 5 mass % or less, even more preferably 3 mass % or less, even more preferably 1 mass % or less in the whole composition.

<Component (E)>

The composition for external preparation for skin of the present invention can further comprise (E) a non-volatile oil. Non-volatility refers to having a mass reduction rate of 1% or less after 1 g of oil is spread on a glass petri dish of 48 mm in diameter, and the glass petri dish is left as it is at 25° C. under normal pressure for 24 hours.

The non-volatile oil of the component (E) is not limited and can be any of a liquid, a paste, and a solid as long as it is used for usual cosmetics. Examples thereof include ester oils, hydrocarbon oils, ether oils, higher alcohols, silicone oils, and solid waxes.

Examples of ester oil include monoester oils such as isononyl isononanoate, isodecyl isononanoate, isotridecyl isononanoate, tricyclodecanemethyl isononanoate, hexyl laurate, octyldodecyl malate, cetyl 2-ethylhexanoate, 2-hexyldecyl 2-ethylhexanoate, isopropyl myristate, 2-hexyldecyl myristate, octyldodecyl myristate, isopropyl palmitate, 2-ethylhexyl palmitate, ethyl isostearate, isopropyl isostearate, isobutyl isostearate, 2-hexyldecyl isostearate, 2-ethylhexyl hydroxystearate, octyldodecyl oleate, oleyl oleate, octyldodecyl ricinoleate, octyl p-methoxycinnamate, and propylene carbonate; diester oils such as di2-etylhexyl succinate, bis-ethoxydiglycol succinate, diol di(caprylate/caprate)propane, neopentyl glycol diisononanoate, neopentyl glycol dicaprate, glyceryl diisostearate, polyglyceryl diisostearate, propanediol diisostearate, diisostearyl malate, di(phytosteryl/octyldodecyl) lauroyl glutamate, di(cholesteryl/behenyl/octyldodecyl) lauroyl glutamate, di(octyldodecyl/phytosteryl/behenyl) lauroyl glutamate, neopentyl glycol di2-ethylhexanoate, and neopentyl glycol dioctanoate; triester oils such as trimethylolpropane triisostearate, glyceryl triisostearate, diglyceryl triisostearate, jojoba oil, trimethylolpropane tri2-etylhexanoate, glyceryl tri2-ethylhexanoate, glyceryl tri(caprylate/caprate), glyceryl trioctanoate, tritridecyl trimeritoate, macadamia nut oil, olive oil, castor oil, jojoba oil, avocado oil, and sunflower oil; pentaerythrityl tetraoctanoate, diglyceryl tetraisostearate, dipentaerythrityl tetraisostearate, and pentaerythrit tetraisostearate.

Examples of hydrocarbon oils include squalane, liquid paraffin, liquid isoparaffin, polybutene, hydrogenated polyisobutene, hydrogenated polydecene, and Vaseline.

Examples of ether oils include cetyl dimethylbutyl ether, and dicaprylyl ether.

Examples of higher alcohols include those having a straight or branched alkyl or alkenyl group having 10 to 24 carbon atoms, and examples thereof include lauryl alcohol, myristyl alcohol, isocetyl alcohol, isostearyl alcohol, 2-octyldodecanol, and oleyl alcohol.

Examples of silicone oils include polydimethylsiloxane, methyl phenyl polysiloxane, methyl hydrogen polysiloxane, acryl-modified silicone, and fluorine-modified silicone.

Solid waxes are oily components which are solid at 25° C., and examples thereof include plant waxes such as candelilla wax, rice bran wax, sunflower wax, carnauba wax, and wood wax; animal waxes such as beeswax and whale wax; mineral waxes such as montan wax and ozokerite; petroleum waxes such as microcrystalline wax, paraffin, and ceresin; synthetic waxes such as hydrogenated castor oil, hydrogenated jojoba oil, 12-hydroxystearate, stearate amide, anhydrous phthalic imide, silicone wax, fluorine wax, polyethylene wax, and synthetic beeswax; fatty acids such as lauric acid, myristic acid, palmitic acid, stearic acid, behenic acid, and lanolin fatty acid; and higher alcohols such as cetyl alcohol, stearyl alcohol, behenyl alcohol, and hydrogenated dilinoleyl alcohol.

In view of achieving a uniform, nice-looking, natural finish and preventing cloudiness, the component (E) preferably comprises an ester oil, a hydrocarbon oil, or a silicone oil, and among these, a non-volatile oil which is liquid at 25° C. is preferred.

In view of achieving a uniform, nice-looking, natural finish and preventing cloudiness, the component (E) preferably comprises at least one or more (E-1) ester oils, more preferably monoester oils, diester oils, or triester oils, even more preferably at least diester oils, even more preferably diester oils which are liquid at 25° C.

One or more different components (E) can be used in combination, and in view of achieving a uniform, nice-looking, natural finish and preventing cloudiness, the content of the components (E) is preferably 0.1 mass % or more, more preferably 0.2 mass % or more, even more preferably 0.4 mass % or more, and preferably 20 mass % or less, more preferably 15 mass % or less, even more preferably 10 mass % or less, even more preferably 8 mass % or less in the whole composition. Further, the content of the component (E) is preferably from 0.1 to 20 mass %, more preferably from 0.2 to 15 mass %, even more preferably from 0.2 to 10 mass %, even more preferably from 0.4 to 8 mass % in the whole composition.

<Other Components>

In the Present Invention, in View of Maintaining the skin wrinkle-reducing effect and obtaining a use impression of non-stickiness, the content of water is preferably 50 mass % or less, more preferably 30 mass % or less, even more preferably 10 mass % or less, even more preferably 5 mass % or less, even more preferably 1 mass % or less in the whole composition.

In addition to the above-described components, the composition for the external preparation for skin of the present invention can optionally use various components usually used as long as the effect of the present invention is not impaired. Examples of these components include oily components other than described above, water-soluble polymers, antioxidants, ultraviolet absorbers, vitamins, preservatives, pH modifiers, flavors, plant extracts, moisturizers, colorants, cooling sensation agents, antiperspirants, sterilizers, and skin activators.

The composition for external preparation for skin of the present invention can be applied to any forms such as oily compositions and emulsified compositions which can be manufactured by usual methods. The composition for external preparation for skin of the present invention can be applied as a preparation such as a liquid, a milky lotion, a paste, a cream, a gel, a solid, or a sheet.

The composition for external preparation for skin of the present invention can be used for cosmetics, quasi-drugs, and drugs and can be used as skin care cosmetics such as lotions, milky lotions, creams, beauty essences, dispersions, gels, ointments, facial masks, mousses, aerosols, poultices, and cleansing agents; ultraviolet protection cosmetics such as sunscreen milky lotions and sunscreen creams; makeup cosmetics such as makeup bases, foundations, concealers, blushes, eye shadows, mascaras, eyeliners, eyebrows, overcoats, and lipsticks, and the like.

Examples of the container for housing the composition for external preparation for skin include bottles, jars, tubes, pumps, syringe containers, mist containers, and pillow containers.

The composition for external preparation for skin of the present invention is suitable for use as a skin wrinkle-reducing agent.

Regarding the above-described embodiments, the present invention further discloses the following compositions.

<1> A composition for external preparation for skin comprising the following components (A), (B), and (C):

(A) from 1 to 90 mass % of a polymer having a silicone moiety in which a ratio of deformation measured by the following method (1) is 0.3 or more and 1 or less, and in a bend resistance test using a cylindrical mandrel method performed by the following method (2), a minimum diameter of a cylindrical mandrel which causes no cracks in the polymer film is 2 mm or longer and 25 mm or shorter:

Method (1): a 10 mass % hexamethyldisiloxane solution of the polymer is prepared. 0.005 g of the solution is applied to an area of 20 mm width×50 mm length on one side of a polyethylene sheet of 20 mm width×100 mm length×0.03 mm thickness in the length direction from one end of a short side, and the polyethylene sheet is dried in a thermostatic oven set at 40° C. for 10 minutes. Assuming the length of the polyethylene sheet portion coated with the solution as L1 and the length of the polyethylene sheet portion deformed by shrinkage after drying as L2, the value of L2/L1 is defined as a ratio of deformation;

Method (2): A 30 mass % hexamethyldisiloxane solution of the polymer is prepared. The solution is applied to a polyethylene terephthalate film of 50 mm width×100 mm length×0.1 mm thickness using a 200 μm applicator, and the film is dried in a thermostatic oven set at 40° C. for 120 minutes to prepare a test piece. A bend resistance test according to the cylindrical mandrel method defined in JIS K5600-5-1:1999 is performed using the test piece, and the minimum diameter of the cylindrical mandrel which causes no cracks in the polymer film on the test piece is obtained.

(B) a volatile oil having a volatilization rate of 14% or more after drying at 1 atmosphere, 40° C., and R.H. of 60% for 30 minutes, and (C) a polyol, wherein a mass ratio of the component (A) to the component (C), (A)/(C), is from 3 to 200.

<2> The composition for external preparation for skin according to the above <1>, wherein, in the component (A), the ratio of deformation, L2/L1, assessed by the method (1) is preferably 0.5 or more, more preferably 0.6 or more, even more preferably 0.7 or more, even more preferably 0.8 or more, even more preferably 0.85 or more, even more preferably 0.9 or more, even more preferably 0.95.

<3> The composition for external preparation for skin according to the above <1> or <2>, wherein, for the component (A), the minimum diameter of the cylindrical mandrel which causes no cracks in a polymer film which is the component (A) is preferably 20 mm or shorter, more preferably 12 mm or shorter, even more preferably 8 mm or shorter, even more preferably 6 mm or shorter, even more preferably 5 mm or shorter, and preferably 3 mm or longer in a bend resistance test using a cylindrical mandrel method performed by the method (2).

<4> The composition for external preparation for skin according to any one of the above <1> to <3>, wherein, for the component (A), the ratio of the ratio of deformation obtained by the method (1) to the minimum diameter (mm) of the mandrel obtained by the method (2) [(ratio of deformation)/(minimum diameter of the mandrel)] is preferably 0.01 or more, more preferably 0.02 or more, even more preferably 0.10 or more, even more preferably 0.15 or more, and preferably 0.5 or less, more preferably 0.4 or less.

<5> The composition for external preparation for skin according to any one of the above <1> to <4>, wherein the component (A) is preferably a silicone-modified polymer, more preferably a silicone-modified polymer containing a norbornane moiety, a silicone-modified Pullulan, a silicic acid compound containing a silicone moiety, or a silicone dendrimer.

<6> The composition for external preparation for skin according to any one of the above <1> to <5>, wherein the component (A) is preferably a silicone-modified polymer containing a norbornane moiety, more preferably a polymer having a repeating unit of the following formula (1) or (2):

(1)

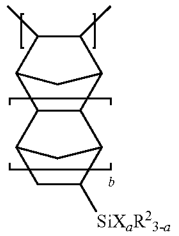

wherein $R^2$ is each independently an alkyl group having one or more and 12 or less carbon atoms, and X is a group of the following formula (i). a is an integer of 1 or more and 3 or less, and b is an integer of 0 or more and 2 or less.

(i)

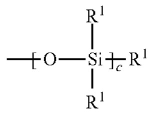

wherein $R^1$ is the same as described above, and c is an integer of 1 or more and 5 or less.

(2)

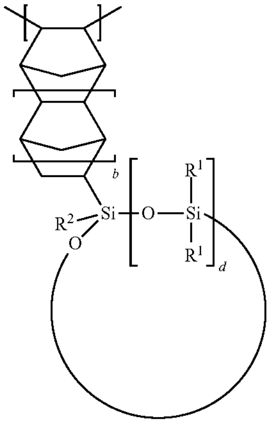

wherein $R^1$, $R^2$, and b are the same as described above, and d is an integer of 2 or more and 5 or less.

<7> The composition for external preparation for skin according to any one of the above <1> to <6>, wherein the component (A) is preferably a silicone-modified polymer containing a norbornane moiety, more preferably a silicone-modified polynorbornene, even more preferably a silicone-modified polynorbornene of the following formula (6):

(6)

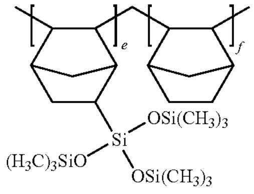

wherein e and f are the numbers of repeating units and each independently an integer of 1 or more.

<8> The composition for external preparation for skin according to the above <7>, wherein, in the formula (6), a ratio of e and f, e/f, is preferably from 20/80 to 90/10 (mol/mol), more preferably from 30/70 to 80/20 (mol/mol), even more preferably from 50/50 to 70/30 (mol/mol).

<9> The composition for external preparation for skin according to any one of the above <1> to <8>, wherein the component (A) is preferably one or more selected from the group consisting of silicone-modified polynorbornenes, silicone-modified Pullulans, trimethylsiloxysilicic acid, trifluoropropyldimethyl/trimethylsiloxysilicic acid, and acrylic silicone dendrimers, more preferably one or more selected from the group consisting of silicone-modified polynorbornenes, silicone-modified Pullulans, trimethylsiloxysilicic acid, and trifluoropropyldimethyl/trimethylsiloxysilicic acid, even more preferably one or more selected from the group consisting of silicone-modified polynorbornenes and silicone-modified Pullulans, even more preferably a silicone-modified polynorbornene.

<10> The composition for external preparation for skin according to any one of the above <1> to <9>, wherein a content of the component (A) is preferably 2 mass % or more, more preferably 4 mass % or more, even more preferably 5 mass % or more, and preferably 25 mass % or less, more preferably 20 mass % or less, even more preferably 18 mass % or less in the whole composition.

<11> The composition for external preparation for skin according to any one of the above <1> to <10>, wherein, in the component (B), the volatilization rate after drying at 1 atmosphere, 40° C., and R.H. of 60% for 30 minutes is preferably 18% or more, more preferably 25% or more, even more preferably 30% or more, even more preferably 45% or more, even more preferably 65% or more, even more preferably 80% or more, even more preferably 95% or more.

<12> The composition for external preparation for skin according to any one of the above <1> to <11>, wherein the component (B) is preferably one or more selected from the group consisting of hydrocarbon oils and silicone oils, more preferably one or more selected from the group consisting of isododecane, hexamethyldisiloxane, methyl trimethicone, and polydimethylsiloxane having kinematic viscosity of 2 cSt or less at 25° C., even more preferably one or more selected from the group consisting of isododecane, hexamethyldisiloxane, and polydimethylsiloxane having kinematic viscosity of 1.5 cSt or less at 25° C., even more preferably one or more selected from the group consisting of hexamethyldisiloxane and polydimethylsiloxane having kinematic viscosity of 1 cSt or less at 25° C., even more preferably hexamethyldisiloxane.

<13> The composition for external preparation for skin according to any one of the above <1> to <12>, wherein a content of the component (B) is preferably 1 mass % or more, more preferably 30 mass % or more, even more preferably 50 mass % or more, even more preferably 70 mass % or more, even more preferably 72 mass % or more, and preferably 98 mass % or less, more preferably 97 mass % or less, even more preferably 94 mass % or less, even more preferably 92 mass % or less, even more preferably 90 mass % or less in the whole composition.

<14> The composition for external preparation for skin according to any one of the above <1> to <13>, wherein a mass ratio of the component (A) to the component (B), (A)/(B), is preferably 0.02 or more, more preferably 0.03 or more, even more preferably 0.04 or more, even more preferably 0.05 or more, even more preferably 0.1 or more, and preferably 1 or less, more preferably 0.7 or less, even more preferably 0.4 or less, even more preferably 0.25 or less.

<15> The composition for external preparation for skin according to any one of the above <1> to <14>, wherein the component (C) is preferably one or more selected from the group consisting of glycols, glycerins, and saccharides, and more preferably comprises one or more selected from the group consisting of propylene glycol, butylene glycol, glycerin, polypropylene glycol, and sorbitol.

<16> The composition for external preparation for skin according to any one of the above <1> to <15>, wherein a content of the component (C) is preferably 0.1 mass % or more, more preferably 0.2 mass % or more, even more preferably 0.3 mass % or more, even more preferably 0.4 mass % or more, and preferably 20 mass % or less, more preferably 10 mass % or less, even more preferably 6 mass % or less, even more preferably 4.5 mass % or less in the whole composition.

<17> The composition for external preparation for skin according to any one of the above <1> to <16>, wherein a mass ratio of the component (A) to the component (C), (A)/(C), is preferably 4 or more, more preferably 5 or more, and preferably 100 or less, more preferably 50 or less, even more preferably 34 or less.

<18> A composition for external preparation for skin comprising the following components (A), (B), and (C):

(A) from 1 to 30 mass % of one or more selected from the group consisting of silicone-modified polynorbornenes and silicone-modified Pullulans, (B) from 1 to 98 mass % of a volatile oil having a volatilization rate of 14% or more after drying at 1 atmosphere, 40° C., and R.H. of 60% for 30 minutes, and (C) from 0.1 to 20 mass % of a polyol, wherein a mass ratio of the component (A) to the component (C), (A)/(C), is from 3 to 200.

<19> A composition for external preparation for skin comprising the following components (A), (B), and (C):

(A) from 1 to 30 mass % of a silicone-modified polynorbornene, (B) from 1 to 98 mass % of a volatile oil having a volatilization rate of 14% or more after drying at 1 atmosphere, 40° C., and R.H. of 60% for 30 minutes, and (C) from 0.1 to 20 mass % of a polyol, wherein a mass ratio of the component (A) to the component (C), (A)/(C), is from 3 to 200.

<20> A composition for external preparation for skin comprising the following components (A), (B), and (C):

(A) from 4 to 20 mass % of one or more selected from the group consisting of silicone-modified polynorbornenes and silicone-modified Pullulans, (B) from 70 to 92 mass % of a volatile oil having a volatilization rate of 14% or more after drying at 1 atmosphere, 40° C., and R.H. of 60% for 30 minutes, and (C) from 0.2 to 10 mass % of a polyol, wherein a mass ratio of the component (A) to the component (C), (A)/(C), is from 3 to 100.

<21> A composition for external preparation for skin comprising the following components (A), (B), and (C):

(A) from 4 to 20 mass % of a silicone-modified polynorbornene, (B) from 70 to 92 mass % of a volatile oil having a volatilization rate of 14% or more after drying at 1 atmosphere, 40° C., and R.H. of 60% for 30 minutes, and (C) from 0.2 to 10 mass % of a polyol, wherein a mass ratio of the component (A) to the component (C), (A)/(C), is from 3 to 100.

<22> The composition for external preparation for skin according to any one of the above <1> to <21>, preferably further comprising a surfactant, more preferably a nonionic surfactant, and even more preferably a nonionic surfactant having HLB of from 1 to 7.

<23> The composition for external preparation for skin according to the above <22>, wherein a content of the nonionic surfactant is preferably 30 mass % or less, more preferably 10 mass % or less, even more preferably 5 mass % or less, even more preferably 3 mass % or less, even more preferably 1 mass % or less in the whole composition.

<24> The composition for external preparation for skin according to any one of the above <1> to <23>, preferably further comprising a non-volatile oil, more preferably one or more selected from the group consisting of ester oils, hydrocarbon oils, and silicones, even more preferably at least an ester oil, and even more preferably at least a diester oil.

<25> The composition for external preparation for skin according to the above <24>, wherein a content of the non-volatile oil is preferably 0.1 mass % or more, more preferably 0.2 mass % or more, even more preferably 0.4 mass % or more, and preferably 20 mass % or less, more preferably 15 mass % or less, even more preferably 10 mass % or less, even more preferably 8 mass % or less in the whole composition.

<26> The composition for external preparation for skin according to any one of the above <1> to <25>, wherein a content of water is preferably 50 mass % or less, more preferably 30 mass % or less, even more preferably 10 mass % or less, even more preferably 5 mass % or less, even more preferably 1 mass % or less in the whole composition.

<27> Use of the composition for external preparation for skin according to any one of the above <1> to <26> as a skin wrinkle-reducing agent.

EXAMPLES

The present invention is described below with reference to examples, but the scope of the present invention is not limited to these examples. Of note, various measurements and assessments were performed by the following methods in the examples.

(Number Average Molecular Weight (Mn))

The number average molecular weight of a polymer was measured under the following conditions by gel filtration chromatography (GPC) using polystyrene as a reference substance.

Measuring device: HLC-8320GPC (manufactured by Tosoh Corporation)

Columns: K-806L (Shodex brand column manufactured by Showa Denko), two columns in series Detector: RI Eluent: 1 mmol/L-FARMIN DM20 (manufactured by Kao Corporation)/$CHCl_3$ Flow rate: 1.0 mL/min Column temperature: 40° C.

(Ratio of Deformation)

A 10 mass % hexamethyldisiloxane solution of a polymer which is the component (A) used for each composition was prepared. 0.005 g of this solution was applied to an area of 20 mm width×50 mm length (a portion of 2 shown in FIG. 1 (*a*)) on one side of a polyethylene sheet 1 of 20 mm width (W)×100 mm length (L0)×0.03 mm thickness ("LL film" manufactured by Enshu Chemical Industries Inc.) shown in FIG. 1 (*a*) in the length direction from one end 1*a* of a short side of the polyethylene sheet 1, and the polyethylene sheet was dried in a thermostatic oven set at 40° C. for 10 minutes. Assuming the length of the polyethylene sheet portion coated with the solution as L1 (50 mm) and the length of the polyethylene sheet portion deformed (curled) by shrinkage after drying as L2 in the polyethylene sheet after drying (FIG. 1 (*b*)), L2/L1 was calculated, and the value was defined as a ratio of deformation of the polymer. L2 was obtained as the mean of values measured on two long sides of the polyethylene sheet 1.

(Bend Resistance)

A 30 mass % hexamethyldisiloxane solution of a polymer which is the component (A) used for each composition was prepared. This solution was applied to a polyethylene terephthalate film ("Lumirror 100T60" manufactured by Toray Industries, Inc.) of 50 mm width×100 mm length×0.1 mm thickness using a 200 μm applicator, and the polyethylene terephthalate film was dried in a thermostatic oven set at 40° C. for 120 minutes to prepare a polymer film-added film (test piece).

Using the obtained test piece, a bend resistance test was performed in accordance with a cylindrical mandrel method defined in JIS K5600-5-1:1999. A bend resistance test was performed with a type 1 bend tester (Bend Tester Model 266 manufactured by Erichsen Inc.) using cylindrical mandrels of 32 mm, 25 mm, 20 mm, 16 mm, 12 mm, 10 mm, 8 mm, 6 mm, 4 mm, 3 mm, and 2 mm in diameter sequentially, starting with a cylindrical mandrel of the longest diameter, while the polymer film side face of the test piece was allowed to face outside. The test was stopped at a time point when a crack occurred in the polymer film, and the minimum diameter of the cylindrical mandrel (mm) with which a crack did not occur was obtained as the value of bend resistance. A smaller value of this minimum diameter means better bend resistance.

(Volatilization Rate)

0.5 g of the sample was placed in a glass petri dish of 40 mm in diameter and left and dried on a hot plate set at 40° C. in an environment of 1 atmosphere and R.H. of 60% for 30 minutes. Assuming the sample mass before drying as $W_0$ (g) and the sample mass after drying as $W_1$ (g), the volatilization rate (%) was defined as a value of $\{(W_0-W_1)/W_0\}\times 100$. A larger value of this volatilization rate means a faster volatilization speed and easier drying.

(Wrinkle-Reducing Effect)

Figure 2:
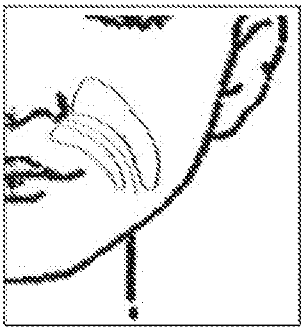
FIG. 2 shows how each composition for external preparation for skin is applied when a wrinkle-reducing effect thereof is assessed in the examples.

Five expert panelists applied 0.2 g of each composition with fingers to nasolabial folds around the mouth on a half side of the face while pinching them in a form shown in FIG. 2. After drying at room temperature (25° C.) for 10 minutes, sensory evaluation was performed with the following criteria to assess the wrinkle-reducing effect. The result was expressed as the sum of scores given by the five panelists.

5: Wrinkles have become considerably thinner.
4: Wrinkles have become thinner.
3: Wrinkles have become slightly thinner.
2: Wrinkles have remained and hardly changed.
1: Wrinkles are unchanged.

(State of Thickness of Coating Film after Coating and Drying)

Five expert panelists applied each composition to the skin, and after drying, sensory evaluation was performed with the following criteria to assess the state of the thickness of the coating film. The result was expressed as the sum of scores given by the five panelists.

5: There is no unevenness in the thickness.
4: There is almost no unevenness in the thickness.
3: There is some unevenness in the thickness.
2: There is unevenness in the thickness.
1: Unevenness in the thickness is significant.

(State of Cloudiness after Coating and During Drying)

Five expert panelists applied each composition to the skin, and during drying, sensory evaluation was performed with the following criteria to assess the state of cloudiness. The result was expressed as the sum of scores given by the five panelists.

5: The coating film does not look white.
4: The coating film does not look very white.
3: Part of the coating film looks slightly white.
2: Part of the coating film looks white.
1: Whole the coating film looks white.

Examples 1 to 14, Comparative Example 1

Compositions for external preparation for skin (liquid) having the compositions shown in Table 1 were manufactured, and the wrinkle-reducing effect, the state of the thickness of the coating film after coating and drying, and the state of cloudiness after coating and during drying were assessed. The results are shown with the compositions in Table 1.

(Manufacturing Method)

An oil phase component obtained by mixing the components (A), (B), and (C) was dispersed with a disperser and stirred with a homo mixer to obtain compositions for external preparation for skin.

TABLE 1

| Component (mass %) | | Raw material name | Examples 1 | 2 | 3 | 4 |
|---|---|---|---|---|---|---|
| Component (A) | Norbornene/tris(trimethylsiloxy)silylnorbornene copolymer solid content *1 | NBN-30-ID manufactured by Shin-Etsu Chemical Co., Ltd | 13.0 | 130 | 13.0 | 13.0 |
| | Silicone-modified Pullulan solid content *2 | TSPL-30-ID manufactured by Shin-Etsu Chemical Co., Ltd | | | | |
| | Trimethylsiloxysilicic acid solid content *3 | X21-5595 manufactured by Shin-Etsu Chemical Co., Ltd | | | | |
| Component (B) | Hexamethyldisiloxane | KF-96L-0.65cs manufactured by Shin-Etsu Chemical Co., Ltd. | 53.7 | 52.7 | 51.3 | 50.7 |
| | Isododecane | Marukasol R manufactured by Maruzen Petrochemical Co., Ltd. | 30.3 | 30.3 | 30.3 | 30.3 |
| Component (C) | Propylene glycol | | | | | |
| | Butylene glycol | | | | | |
| | Glycerin | | 1.0 | 1.0 | 0.4 | 1.0 |
| | Polypropylene glycol | | | | | |
| | Sorbitol | | | | | |
| Component (D) | Polyether-modified silicone | SH3775M manufactured by Dow Corning Toray Co., Ltd. | | 1.0 | 1.0 | 1.0 |
| Component (E) | Polyglyceryl diisostearate-2 | Cosmol 42V manufactured by The Nisshin OilliO Group, Ltd | | | 20 | 2.0 |

TABLE 1-continued

| | | | | | | |
|---|---|---|---|---|---|---|
| Other components | Water | | 2.0 | 2.0 | 2.0 | 2.0 |
| | Total | | 100.0 | 100.0 | 100.0 | 100.0 |
| | (A) | | 13.0 | 130 | 13.0 | 13.0 |
| | (B) | | 84.0 | 83.0 | 81.6 | 81.0 |
| | (C) | | 1.0 | 1.0 | 0.4 | 1.0 |
| | (D) | | — | 1.0 | 1.0 | 1.0 |
| | (E) | | — | — | 2.0 | 2.0 |
| | (A)/(C) | | 13.0 | 13.0 | 32.5 | 13.0 |
| | (A)/(B) | | 0.15 | 0.16 | 0.16 | 0.16 |
| Polymer property | Ratio of deformation measured by method (1) | | 1.0 | 1.0 | 1.0 | 1.0 |
| | Bend resistance measured by method (2) (Minimum diameter of the cylindrical mandrel which causes no cracks in the polymer film: mm) | | 4 | 4 | 4 | 4 |
| | Ratio of deformation/minimum diameter of the mandrel | | 0.250 | 0.250 | 0.250 | 0.250 |
| Component (B) Property | Volatilization rate (%) | | 82.5 | 82.5 | 79.6 | 79.4 |
| Assessment | Wrinkle-reducing effect | | 25 | 25 | 25 | 25 |
| | State of thickness of coating film after coating and drying | | 20 | 21 | 22 | 24 |
| | State of cloudiness after coating and during drying | | 20 | 22 | 23 | 24 |

| | | | Examples | | | |
|---|---|---|---|---|---|---|
| | Component (mass %) | Raw material name | 5 | 6 | 7 | 8 |
| Component (A) | Norbornene/tris(trimethylsiloxy)silylnorbornene copolymer solid content *1 | NBN-30-ID manufactured by Shin-Etsu Chemical Co., Ltd | 13.0 | 13.0 | 5.0 | 18.0 |
| | Silicone-modified Pullulan solid content *2 | TSPL-30-ID manufactured by Shin-Etsu Chemical Co., Ltd | | | | |
| | Trimethylsiloxysilicic acid solid content *3 | X21-5595 manufactured by Shin-Etsu Chemical Co., Ltd | | | | |
| Component (B) | Hexamethyldisiloxane | KF-96L-0.65cs manufactured by Shin-Etsu Chemical Co., Ltd. | 48.7 | 47.7 | 77.8 | 30.5 |
| | Isododecane | Marukasol R manufactured by Maruzen Petrochemical Co., Ltd. | 30.3 | 30.3 | 11.7 | 42.0 |
| Component (C) | Propylene glycol | | | | | |
| | Butylene glycol | | | | | |
| | Glycerin | | 3.0 | 4.0 | 0.5 | 4.5 |
| | Polypropylene glycol | | | | | |
| | Sorbitol | | | | | |
| Component (D) | Polyether-modified silicone | SH3775M manufactured by Dow Corning Toray Co., Ltd. | 1.0 | 1.0 | 1.0 | 1.0 |
| Component (E) | Polyglyceryl diisostearate-2 | Cosmol 42V manufactured by The Nisshin OilliO Group, Ltd | 2.0 | 2.0 | 2.0 | 2.0 |
| Other components | Water | | 2.0 | 2.0 | 2.0 | 2.0 |
| | Total | | 100.0 | 100.0 | 100.0 | 100.0 |
| | (A) | | 13.0 | 13.0 | 5.0 | 180 |
| | (B) | | 79.0 | 78.0 | 89.5 | 72.5 |
| | (C) | | 3.0 | 4.0 | 0.5 | 4.5 |
| | (D) | | 1.0 | 1.0 | 1.0 | 1.0 |
| | (E) | | 2.0 | 2.0 | 2.0 | 2.0 |
| | (A)/(C) | | 4.3 | 3.3 | 10.0 | 4.0 |
| | (A)/(B) | | 0.16 | 0.17 | 0.06 | 0.25 |
| Polymer property | Ratio of deformation measured by method (1) | | 1.0 | 1.0 | 1.0 | 1.0 |
| | Bend resistance measured by method (2) (Minimum diameter of the cylindrical mandrel which causes no cracks in the polymer film: mm) | | 4 | 4 | 4 | 4 |
| | Ratio of deformation/minimum diameter of the mandrel | | 0.250 | 0.250 | 0.250 | 0.250 |
| Component (B) Property | Volatilization rate (%) | | 78.8 | 77.6 | 97.6 | 64.2 |
| Assessment | Wrinkle-reducing effect | | 25 | 25 | 20 | 25 |
| | State of thickness of coating film after coating and drying | | 23 | 21 | 24 | 20 |
| | State of cloudiness after coating and during drying | | 22 | 21 | 25 | 20 |

| | | | Examples | | | |
|---|---|---|---|---|---|---|
| | Component (mass %) | Raw material name | 9 | 10 | 11 | 12 |
| Component (A) | Norbornene/tris(trimethylsiloxy)silylnorbornene copolymer solid content *1 | NBN-30-ID manufactured by Shin-Etsu Chemical Co., Ltd | 13.0 | 13.0 | 13.0 | 13.0 |
| | Silicone-modified Pullulan solid content *2 | TSPL-30-ID manufactured by Shin-Etsu Chemical Co., Ltd | | | | |
| | Trimethylsiloxysilicic acid solid content *3 | X21-5595 manufactured by Shin-Etsu Chemical Co., Ltd | | | | |

TABLE 1-continued

| | | | | | | |
|---|---|---|---|---|---|---|
| Component (B) | Hexamethyldisiloxane | KF-96L-0.65cs manufactured by Shin-Etsu Chemical Co., Ltd. | 50.7 | 50.7 | 50.7 | 50.7 |
| | Isododecane | Marukasol R manufactured by Maruzen Petrochemical Co., Ltd. | 30.3 | 30.3 | 30.3 | 303 |
| Component (C) | Propylene glycol | | 1.0 | | | |
| | Butylene glycol | | | 1.0 | | |
| | Glycerin | | | | | |
| | Polypropylene glycol | | | | 1.0 | |
| | Sorbitol | | | | | 1.0 |
| Component (D) | Polyether-modified silicone | SH3775M manufactured by Dow Corning Toray Co., Ltd. | 1.0 | 1.0 | 1.0 | 1.0 |
| Component (E) | Polyglyceryl diisostearate-2 | Cosmol 42V manufactured by The Nisshin OilliO Group, Ltd | 2.0 | 2.0 | 2.0 | 2.0 |
| Other components | Water | | 2.0 | 2.0 | 2.0 | 2.0 |
| | Total | | 100.0 | 100.0 | 100.0 | 100.0 |
| | (A) | | 13.0 | 13.0 | 13.0 | 13.0 |
| | (B) | | 81.0 | 81.0 | 81.0 | 81.0 |
| | (C) | | 1.0 | 1.0 | 1.0 | 1.0 |
| | (D) | | 1.0 | 1.0 | 1.0 | 1.0 |
| | (E) | | 2.0 | 2.0 | 2.0 | 2.0 |
| | (A)/(C) | | 13.0 | 13.0 | 13.0 | 13.0 |
| | (A)/(B) | | 0.16 | 0.16 | 0.16 | 0.16 |
| Polymer property | Ratio of deformation measured by method (1) | | 1.0 | 1.0 | 1.0 | 1.0 |
| | Bend resistance measured by method (2) (Minimum diameter of the cylindrical mandrel which causes no cracks in the polymer film: mm) | | 4 | 4 | 4 | 4 |
| | Ratio of deformation/minimum diameter of the mandrel | | 0.250 | 0.250 | 0.250 | 0.250 |
| Component (B) Property | Volatilization rate (%) | | 79.4 | 79.4 | 79.4 | 79.4 |
| Assessment | Wrinkle-reducing effect | | 25 | 25 | 25 | 25 |
| | State of thickness of coating film after coating and drying | | 23 | 24 | 20 | 20 |
| | State of cloudiness after coating and during drying | | 24 | 23 | 21 | 20 |

| | | | Examples | | Comp Ex. |
|---|---|---|---|---|---|
| | Component (mass %) | Raw material name | 13 | 14 | 1 |
| Component (A) | Norbornene/tris(trimethylsiloxy)silylnorbornene copolymer solid content *1 | NBN-30-ID manufactured by Shin-Etsu Chemical Co., Ltd | | | 13.0 |
| | Silicone-modified Pullulan solid content *2 | TSPL-30-ID manufactured by Shin-Etsu Chemical Co., Ltd | 13.0 | | |
| | Trimethylsiloxysilicic acid solid content *3 | X21-5595 manufactured by Shin-Etsu Chemical Co., Ltd | | 13.0 | |
| Component (B) | Hexamethyldisiloxane | KF-96L-0.65cs manufactured by Shin-Etsu Chemical Co., Ltd. | 50.7 | 50.7 | 51.7 |
| | Isododecane | Marukasol R manufactured by Maruzen Petrochemical Co., Ltd. | 30.3 | 30.3 | 30.3 |
| Component (C) | Propylene glycol | | | | |
| | Butylene glycol | | | | |
| | Glycerin | | 1.0 | 1.0 | |
| | Polypropylene glycol | | | | |
| | Sorbitol | | | | |
| Component (D) | Polyether-modified silicone | SH3775M manufactured by Dow Corning Toray Co., Ltd. | 1.0 | 1.0 | 1.0 |
| Component (E) | Polyglyceryl diisostearate-2 | Cosmol 42V manufactured by The Nisshin OilliO Group, Ltd | 2.0 | 2.0 | 2.0 |
| Other components | Water | | 2.0 | 2.0 | 2.0 |
| | Total | | 100.0 | 100.0 | 100.0 |
| | (A) | | 13.0 | 13.0 | 13.0 |
| | (B) | | 81.0 | 81.0 | 82.0 |
| | (C) | | 1.0 | 1.0 | 0.0 |
| | (D) | | 1.0 | 1.0 | 1.0 |
| | (E) | | 2.0 | 2.0 | 2.0 |
| | (A)/(C) | | 13.0 | 13.0 | — |
| | (A)/(B) | | 0.16 | 0.16 | 0.16 |
| Polymer property | Ratio of deformation measured by method (1) | | 0.9 | 0.8 | 1.0 |
| | Bend resistance measured by method (2) (Minimum diameter of the cylindrical mandrel which causes no cracks in the polymer film: mm) | | 8 | 25 | 4 |
| | Ratio of deformation/minimum diameter of the mandrel | | 0.113 | 0.032 | 0.250 |
| Component (B) Property | Volatilization rate (%) | | 79.4 | 79.4 | 81.5 |
| Assessment | Wrinkle-reducing effect | | 18 | 14 | 25 |
| | State of thickness of coating film after coating and drying | | 17 | 17 | 7 |
| | State of cloudiness after coating and during drying | | 16 | 19 | 6 |

*1 to *3 in Table 1 are as follows:

1: "NBN-30-ID" (an isododecane solution of a norbornene/tris(trimethylsiloxy)silylnorbornene copolymer with e/f of 60/40 (mol/mol) in the following formula (6) and Mn of 360,000; effective concentration: 30 mass %) manufactured by Shin-Etsu Chemical Co., Ltd. was dried under reduced pressure at 50° C. for 12 hours, and the obtained solid content was used.

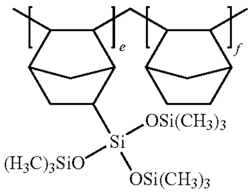

(6)

*2: "TSPL-30-ID" (an isododecane solution of tri(trimethylsiloxy)silyl propyl carbamide acid Pullulan; effective concentration: 30 mass %) manufactured by Shin-Etsu Chemical Co., Ltd. was dried under reduced pressure at 50° C. for 12 hours, and the obtained solid content was used.

*3: "X21-5595" (an isododecane solution of trimethylsiloxysilicic acid; effective concentration: 60 mass %) manufactured by Shin-Etsu Chemical Co., Ltd. was dried under reduced pressure at 50° C. for 12 hours, and the obtained solid content was used.

Examples 15 to 17

As in Examples 1 to 14, compositions for external preparation for skin having the compositions shown in Table 2 were manufactured.

All the obtained compositions for external preparation for skin can improve wrinkles, have no unevenness in the thickness of the coating film, and prevent cloudiness after coating and during drying.

TABLE 2

| | Component (mass %) | Raw material name | Examples 15 | 16 | 17 |
|---|---|---|---|---|---|
| Component (A) | Norbornene/tris(trimethylsiloxy)silylnorbornene copolymer solid content *1 | NBN-30-ID manufactured by Shin-Etsu Chemical Co., Ltd. | 13.0 | 13.0 | |
| | Trifluoroalkyldimethyl trimethylsiloxysilicic acid solid content *4 | XS66-B8826 manufactured by Momentive Performance Materials Japan LLC. | | | 13.0 |
| Component (B) | Hexamethyldisiloxane | KF-96L-0.65cs manufactured by Shin-Etsu Chemical Co., Ltd. | 34.7 | 49.3 | 49.7 |
| | Octamethyltrisiloxane | KF-96L-1cs manufactured by Shin-Etsu Chemical Co., Ltd. | 15.0 | | |
| | Isododecane | Marukasol R manufactured by Maruzen Petrochemical Co., Ltd. | 30.3 | 30.3 | 30.3 |
| Component (C) | Propylene glycol | | | 0.3 | |
| | Butylene glycol | | | 0.3 | |
| | Glycerin | | 1.0 | 0.4 | 1.0 |
| Component (D) | Polyether-modified silicone | SH3775M manufactured by Dow Corning Toray Co., Ltd. | 2.0 | 2.0 | 2.0 |
| Component (E) | Polyglyceryl diisostearate-2 | Cosmol 42V manufactured by The Nisshin OilliO Group, Ltd. | 2.0 | 0.3 | 2.0 |
| | Isotridecyl isononanoate | Salacos 913 manufactured by The Nisshin OilliO Group, Ltd. | | 0.3 | |
| | Glyceryl tri(caprylate/caprate/myristate/stearate) | Salacos 334 manufactured by The Nisshin OilliO Group, Ltd. | | 0.3 | |
| | Di(cholesteryl/behenyl/octyldodecyl) lauroyl glutamate | Eldew CL-301 manufactured by Ajinomoto Co., Inc. | | 0.3 | |
| | Di(octyldodecyl/phytosteryl/behenyl) lauroyl glutamate | Eldew PS-306 manufactured by Ajinomoto Co., Inc. | | 0.3 | |
| | Hydrogenated polyisobutene | ParLeam EX manufactured by NOF CORPORATION | | 0.3 | |
| | Vaseline | Nomcoat W manufactured by The Nisshin OilliO Group, Ltd. | | 0.3 | |
| | Dimethylpolysiloxane 6cs | KF-96A-6cs manufactured by Shin-Etsu Chemical Co., Ltd. | | 0.3 | |
| Other components | Water | | 2.0 | 2.0 | 2.0 |
| | Total | | 100.0 | 100.0 | 100.0 |
| | (A) | | 13.0 | 13.0 | 13.0 |
| | (B) | | 80.0 | 79.6 | 80.0 |
| | (C) | | 1.0 | 1.0 | 1.0 |
| | (D) | | 2.0 | 2.0 | 2.0 |
| | (E) | | 2.0 | 2.4 | 2.0 |
| | (A)/(C) | | 13.0 | 13.0 | 13.0 |
| | (A)/(B) | | 0.16 | 0.16 | 0.16 |

TABLE 2-continued

| Component (mass %) | | Raw material name | Examples 15 | 16 | 17 |
|---|---|---|---|---|---|
| Polymer property | Ratio of deformation measured by method (1) | | 1.0 | 1.0 | 0.7 |
| | Bend resistance measured by method (2) (Minimum diameter of the cylindrical mandrel which causes no cracks in the polymer film: mm) | | 4 | 4 | 25 |
| | Ratio of deformation/minimum diameter of the mandrel | | 0.250 | 0.250 | 0.028 |
| Component (B) Property | Volatilization rate (%) | | 46.3 | 78.6 | 79.4 |

*4 in Table 2 is as follows.

4: "XS66-B8226" (a cyclopentasiloxane solution of trifluoropropyldimethyl/trimethylsiloxysilicic acid; effective concentration, 50 mass %) manufactured by Momentive Performance Materials Japan LLC was dried under reduced pressure at 50° C. for 12 hours, and the obtained solid was used.

Examples 18 to 19

As in Examples 1 to 14, compositions for external preparation for skin having the compositions shown in Table 3 were manufactured.

All the obtained compositions for external preparation for skin can improve wrinkles, have no unevenness in the thickness of the coating film, and prevent cloudiness after coating and during drying.

TABLE 3

| Component (mass %) | | Raw material name | Examples 18 | 19 |
|---|---|---|---|---|
| Component (A) | Norbornene/tris(trimethylsiloxy)silylnorbornene copolymer solid content *1 | NBN-30-ID manufactured by Shin-Etsu Chemical Co., Ltd. | 13.0 | 13.0 |
| Component (B) | Hexamethyldisiloxane | KF-96L-0.65cs manufactured by Shin-Etsu Chemical Co., Ltd. | 51.3 | 51.3 |
| | Isododecane | Marukasol R manufactured by Maruzen Petrochemical Co., Ltd. | 30.3 | 30.3 |
| Component (C) | Glycerin | | 0.14 | 0.14 |
| Component (D) | Polyether-modified silicone | SH3775M manufactured by Dow Corning Toray Co., Ltd. | 1.0 | 1.0 |
| Component (E) | Polyglyceryl diisostearate-2 | Cosmol 42V manufactured by The Nisshin OilliO Group, Ltd. | 2.26 | 2.26 |
| Other components | Water | | 2.0 | |
| | Dimethicone treated silica | SA-SB-300 (Average particle size 3-7 μm) manufactured by Miyoshi Kasei, Inc. | | 2.0 |
| | Total | | 100.00 | 100.00 |
| | (A) | | 13.0 | 13.0 |
| | (B) | | 81.6 | 81.6 |
| | (C) | | 0.14 | 0.14 |
| | (D) | | 1.0 | 1.0 |
| | (E) | | 2.26 | 2.26 |
| | (A)/(C) | | 92.9 | 92.9 |
| | (A)/(B) | | 0.16 | 0.16 |
| Polymer property | Ratio of deformation measured by method (1) | | 1.0 | 1.0 |
| | Bend resistance measured by method (2) (Minimum diameter of the cylindrical mandrel which causes no cracks in the polymer film: mm) | | 4 | 4 |
| | Ratio of deformation/minimum diameter of the mandrel | | 0.250 | 0.250 |
| Component (B) Property | Volatilization rate (%) | | 79.6 | 79.6 |

Example 20

The composition for external preparation for skin (liquid) having the composition shown in Table 1 was manufactured and filled in a mist container. The composition for external preparation for skin was sprayed from this mist container to the nasolabial folds of the face and the surrounding site, and the wrinkle-reducing effect after drying, the state of the thickness of the coating film after coating and drying, and the state of cloudiness after coating and during drying were assessed. As a result, the wrinkle-reducing effect was excellent, and a nice-looking film having no uneven thickness of the coating film in which cloudiness was prevented was achieved.

REFERENCE SIGN LIST

1 A polyethylene sheet

1*a* One end of a short side of the polyethylene sheet 1

2 A portion coated with a polymer solution

The invention claimed is:

1. A composition for external preparation for skin comprising the following components (A), (B), and (C):

(A) comprises from a norbornene/tris(trimethylsiloxy) silylnorbornene) copolymer, (B) comprises a volatile oil having a volatilization rate of 14% or more after drying at 1 atmosphere, at 40° C., and an R.H. of 60% for 30 minutes, wherein the component (B) comprises one or more selected from the group consisting of isododecane, hexamethyldisiloxane, methyl trimethicone, and polydimethylsiloxane having kinematic viscosity of 2 cSt or less at 25° C., and (C) comprises a polyol, wherein a content of the component (A) is from 13 to 18 mass %;

a content of the component (B) is from 70 to 85 mass %; and a content of the component (C) is from 0.4 to 5 mass %, each based on a total mass of the composition, a mass ratio of the component (A) to the component (C), (A)/(C), is from 3.3 to 34, and the composition is a liquid.

2. The composition for external preparation for skin according to claim 1, wherein the component (C) is one or more selected from the group consisting of glycols, glycerins, and sugar alcohols.

3. The composition for external preparation for skin according to claim 1, wherein a mass ratio of the component (A) to the component (B), (A)/(B), is from 0.16 to 0.25.

4. The composition for external preparation for skin according to claim 1, further comprising (D) a surfactant.

5. The composition for external preparation for skin according to claim 1, further comprising a non-volatile oil.

6. The composition for external preparation for skin according to claim 1, further comprising water.

7. A method of reducing wrinkles, comprising: applying to skin the composition for external preparation for skin according to claim 1.

* * * * *